United States Patent [19]

Konz et al.

[11] Patent Number: 4,547,508
[45] Date of Patent: Oct. 15, 1985

[54] 1-PHENYLISOQUINOLINE DERIVATIVES, PHARMACEUTICAL PRODUCTS CONTAINING THESE COMPOUNDS AND THEIR USE

[75] Inventors: Elmar Konz; Hansjörg Kruse, both of Kelkheim, Fed. Rep. of Germany

[73] Assignee: Hoechst Aktiengesellschaft, Frankfurt, Fed. Rep. of Germany

[21] Appl. No.: 556,684

[22] Filed: Nov. 30, 1983

[30] Foreign Application Priority Data

Dec. 2, 1982 [DE] Fed. Rep. of Germany ....... 3244594

[51] Int. Cl.⁴ .................. A61K 31/445; C07D 401/04
[52] U.S. Cl. ..................................... 514/307; 546/90; 546/144
[58] Field of Search ................... 546/144, 90; 424/258

[56] References Cited

U.S. PATENT DOCUMENTS

| 3,457,265 | 7/1969 | Seeger et al. | 546/144 |
| 3,544,577 | 12/1970 | Seeger et al. | 546/144 |
| 3,891,654 | 6/1975 | Valette | 424/258 |
| 4,386,090 | 5/1983 | Moinet et al. | 546/205 |
| 4,431,851 | 2/1984 | Moinet et al. | 546/144 |

FOREIGN PATENT DOCUMENTS

| 81106884 | 9/1981 | European Pat. Off. |
| 2246307 | 3/1973 | Fed. Rep. of Germany |
| 2210667 | 9/1973 | Fed. Rep. of Germany |
| 80 27252 | 6/1982 | France |
| 1528738 | 10/1978 | United Kingdom |

OTHER PUBLICATIONS

10 Eur. J. Med. Chem. 603 (1975).
Synthesis 281 (1979).
Liebigs Ann. Chem. 1978 (1963).
21 J. Med. Chem. 309 (1978).
12 J. Med. Chem. 851–54 (1969).
2 Handbook of Neurochemistry, 327–64 (1969).
23 Biochemical Pharmac. 3413–22 (1974).
Pictet et al., "Chem. Ber.", vol. 42, 1909, pp. 1973–1989.
Späth et al., "Chem. Ber.", vol. 63, 1930, pp. 134–141.
Grierson et al., "J. Amer. Chem. Soc.", vol. 102(3), 1980, pp. 1064–1081.
Miller et al., "J. Amer. Chem. Soc.", vol. 78, 1956, pp. 674–676.
Wright et al., "J. Org. Chem.", vol. 26, 1961, pp. 4057–4060.

*Primary Examiner*—Richard L. Raymond
*Assistant Examiner*—James H. Turnipseed
*Attorney, Agent, or Firm*—Finnegan, Henderson, Farabow, Garrett & Dunner

[57] ABSTRACT

1-Phenylisoquinoline derivatives of the general formula I

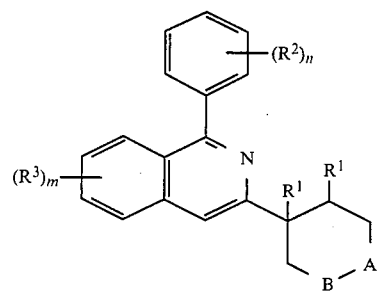

and a process for their preparation are described. They act on the central nervous system, in particular as antidepressants.

3 Claims, No Drawings

1-PHENYLISOQUINOLINE DERIVATIVES, PHARMACEUTICAL PRODUCTS CONTAINING THESE COMPOUNDS AND THEIR USE

According to German Offenlegungsschrift No. 2,246,307, substituted 3-hydroxymethylisoquinolines have spasmolytic properties. 3,4-Dihydroisoquinolines which are substituted in the 3-position by an alkyleneamino group and have analgesic and antidepressant effects are known from German Offenlegungsschrift No. 3,150,876. Isoquinolines having pyridyl substituents in the 3-position (cf. Eur. J. Med. Chem. 10, 603 (1975) are active against Mycoplasma gallisepticum. Dihydropyridines as substituents in the 3-position of isoquinoline are described as coronary dilators in German Offenlegungsschrift No. 2,210,667.

The present invention relates to new 1-phenylisoquinoline derivatives which are substituted in the 3-position by a basic ring and have psychotropic effects, a process for their preparation, pharmaceutical products containing these compounds and their use.

The invention relates to 1-phenylisoquinoline derivatives of the general formula I

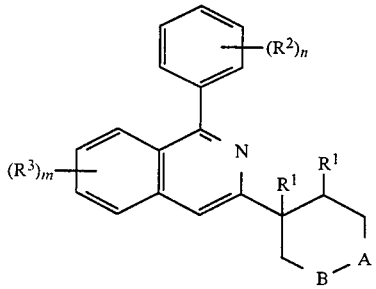

in which m and n, independently of one another, denote one or two, one of A and B is a $CH_2$ and the other is an $N-R^4$ group, $R^4$ being hydrogen, benzyl or a straight-chain or branched, saturated or unsaturated $C_1-C_6$-alkyl radical, and the radicals $R^1$ denote hydrogen or, together, a bond, and $R^2$ denotes hydrogen, halogen, hydroxyl, nitro, amino, $C_1-C_6$-alkyl or $C_1-C_6$-alkoxy radicals, and $R^3$ denotes hydrogen, halogen, hydroxyl, nitro, amino, $C_1-C_6$-alkyl or $C_1-C_6$-alkoxy radicals, or the benzyloxy, methylenedioxy or ethylenedioxy group.

Those compounds of the general formula I are preferred in which m and n, independently of one another, denote one or two, one of A and B is $C_2$ and the other is an $N-R^4$ group, $R_4$ being hydrogen or a straight-chain or branched, saturated or unsaturated $C_1-C_6$-alkyl radical, and the radicals $R^1$ denote hydrogen or, together, a bond, and $R^2$ denotes hydrogen, halogen, hydroxyl, nitro, amino, or a $C_1-C_4$-alkyl or $C_1-C_4$-alkoxy radical, and $R^3$ denotes hydrogen, halogen, hydroxyl, nitro, amino, or a $C_1-C_4$-alkyl or $C_1-C_4$-alkoxy radical.

Those compounds of the formula I are of particular interest in which m and n denote one or two, one of A and b is $CH_2$ and the other is an $N-R^4$ group, $R^4$ being hydrogen or a straight-chain or branched $C_1-C_4$-alkyl radical, in particular the methyl, ethyl, propyl, isopropyl, butyl or isobutyl radical, the radicals $R^1$ denote hydrogen or, together, a bond, $R^2$ denotes hydrogen, fluorine, chlorine, bromine, hydroxyl, amino, methyl, ethyl, methoxy or ethoxy, preferably in the ortho and-/or para-position, and $R^3$ denotes hydrogen, fluorine, chlorine, bromine, hydroxyl, amino, methyl, ethyl, methoxy or ethoxy, preferably in the 6- and/or 7-position.

Those compounds of the formula I are of very particular interest in which m and n denote one, one of A and B is $CH_2$ and the other is an $N-R^4$ group, $R^4$ being hydrogen, methyl, ethyl or propyl, the radicals $R^1$ together denote a bond, $R^2$ denotes hydrogen, fluorine, chlorine, hydroxyl, methyl or methox, preferably in the ortho-position, and $R^3$ denotes hydrogen, fluorine, chlorine, hydroxyl, methyl or methoxy, preferably in the 6- and/or 7-position.

The process for the preparation of the compounds of the general formula I comprises (a) reacting a compound of the general formula II

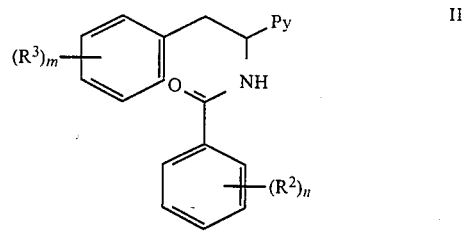

in which m, n, $R^2$ and $R^3$ have the meanings mentioned for the general formula I, and Py denotes the 3- or 4-pyridyl radical, with a dehydrating agent, such as, for example, phorphorus pentoxide or phosphorus oxychloride, in a high-boiling solvent at a temperature between 100° and 220° C., such as, for example, tetralin, diisopropylbenzene, trimethylbenzene, diphenyl ether, diethylene glycol diethyl ether, to give an isoquinoline derivative of the general formula III.

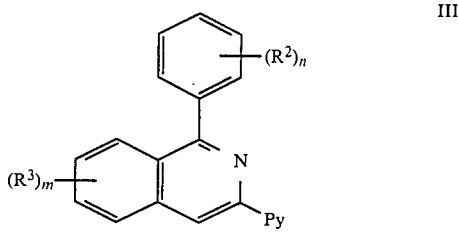

This is then reacted with an alkylating agent of the general formula $Z-R^4$, in which Z denotes iodine, bromine, chlorine, or the mesyl or tosyl radical, and $R^4$ is benzyl or a straight-chain or branched, saturated or unsaturated $C_1-C_6$-alkyl radical, and the resulting quaternary pyridinium salts are reduced with a complex metal hydride to give compounds of the formula I, in which the radicals $R^1$ together represent a bond, and $R^4$ is benzyl or a straight-chain or branched, saturated or unsaturated $C_1-C_6$-alkyl radical, or (b) catalytically reducing a compound of the general formula III to give a compound of the general formula I, in which m, n, $R^2$, $R^3$, A and B have the meanings mentioned for formula I, and the radicals $R^1$ and $R^4$ equal hydrogen, and optionally reacting a compound of the general formula I thus obtained with an alkylating agent of the general formula $Z-R^4$ to give a compound of the general formula I, in which m, n, $R^2$, $R^3$, A and B have the meanings mentioned for formula I, and the radicals $R^1$ denote hydrogen and $R^4$ denotes benzyl or a straight-chain or branched, saturated or unsaturated $C_1$-$C_6$-alkyl radical.

In procedure (a), the compounds II are either converted in one step into completely aromatic isoquinoline derivatives III, or ring closure is first carried out to give the 3,4-dihydro compound IV,

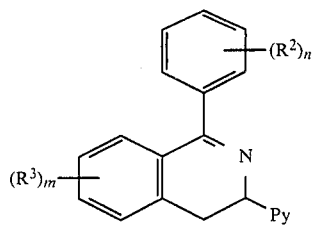

IV in which m, n, $R^2$ and $R^3$ have the meanings indicated for formula I, and Py denotes the 3- or 4-pyridyl radical, and the latter is then dehydrogenated to give the isoquinoline derivative III, in analogy to the details given by A. Pictet and F. W. Kay in Ber. 42, 1973–1989 (1909) or E. Spath, F. Berger and W. Kuntara, Ber. 63, 134–141 (1930).

The compounds III are then alkylated with the alkylating agent Z-$R^4$. The reduction of the quaternary pyridinium salts thus produced is advantageously carried out with lithium aluminum hydride, sodium cyanoborohydride or sodium borohydride in a solvent such as ether, tetrahydrofuran, ethanol, water or in a mixture of these solvents, at temperatures between 0° and 100° C. It is also advantageous to add bases such as sodium hydroxide, as described in the literature (Synthesis 1979, 281; J. Am. Chem. Soc. 102, 1064 (1980); Ann. 1978, 1963).

In order to prepare those compounds of the formula I in which m, n, $R^2$ and $R^3$ have the meanings mentioned for formula I, the radicals $R^1$ together represent a bond, and $R^4$ denotes a hydrogen atom, a compound of the general formula V is converted, with phenyl chloroformate, into the urethane VL

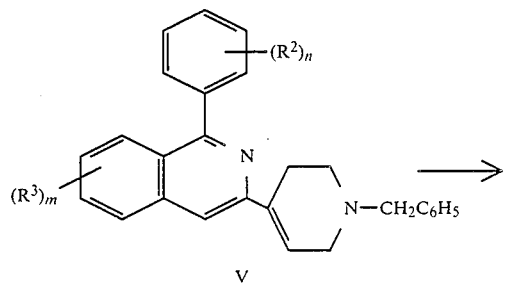

V

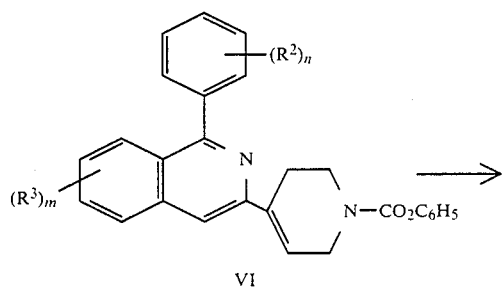

VI

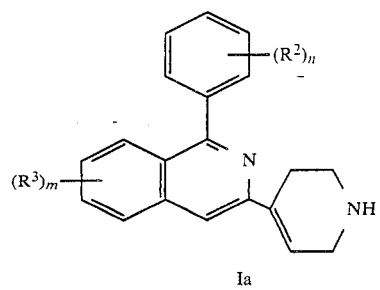

Ia and the latter is then cleaved with dilute sodium hydroxide solution to give a compound of the general formula Ia. This reaction sequence can likewise be carried out with the corresponding 1,2,5,6-tetrahydro-3-pyridyl compounds, and leads to compounds of the general formula Ib in which the radicals $R^1$ together represent a bond, and $R^4$ denotes a hydrogen atom.

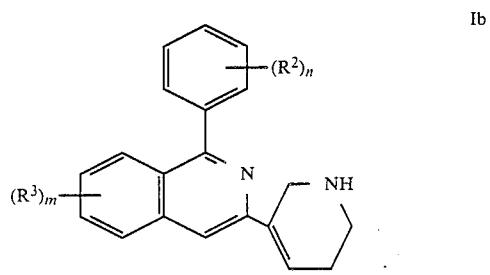

Ib

This reaction is carried out in analogy to J. Org. Chem. 26, 4057, (1961) and J. Med. Chem. 21, 309, (1978).

In procedure (b), the compounds of the general formula III are catalytically hydrogenated, for example with palladium on animal charcoal or with platinum oxide as the catalyst in ethanolic hydrochloric acid at room temperature and under normal pressure, until the theoretical amount of hydrogen has been taken up. By-products formed during this are variable amounts of the tetrahydroisoquinoline compound VII, in which n, m, $R^2$, $R^3$, A and B have the meanings mentioned for formula I and in which the group N-$R^4$ equals N—H,

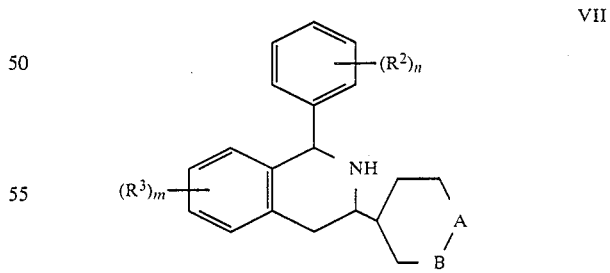

VII which can be separated out by column chromatography, for example on silica gel using chloroform/methanol.

The starting materials of the general formula II are prepared as follows: 3-pyridyl benzyl ketone is obtained from 3-cyanopyridine with benzyl magnesium chloride (cf. Am. Chem. Soc. 78, 674–676 (1956)).

The analogous reaction with 4-cyanopyridine provides 4-pyridyl benzyl ketone.

The same ketones can be obtained by the condensation of ethyl phenylacetate or of benzyl cyanides with ethyl nicotinate or ethyl isonicotinate, which is described in J. Med. Chem. 12, (1969), 851–854.

The ketones thus obtained react with hydroxylamine to give the oximes which are catalytically reduced to give the amines. The reaction with the appropriate acid chlorides provides the amides of the formula II.

The compounds of the general formula I according to the invention act on the central nervous system. In particular, they abolish the ptosis brought about by tetrabenazine in mice. In addition, these compounds inhibit the reuptake of norepinephrine in synaptosomes. By reason of these properties, the compounds according to the invention can be used as active ingredients in medicaments having antidepressant effects.

To assess the actions of the compounds of the invention, pharmacological tests were carried out as follows:

A. Acute toxicity in the mouse after intraperitoneal administration ($ALD_{50}$)

The experimental animals used were male mice (Gassner, NMRI) of body weight 20–30 g. 6 animals were tested in each group. The compounds were suspended in 1% strength methylhydroxyethylcellulose (MH) and administered intraperitoneally (i.p.) to the animals in a volume of 10 ml/kg of body weight. The compounds according to the invention were administered in doses of 3, 10, 30 and 100 mg/kg i.p.

The acute lethal dose ($ALD_{50}$) was determined graphically from the number of animals which died within 24 hours after administration of the compound. This is given in the Table 1 below.

B. Prevention of the ptosis induced by tetrabenazine in mice after intraperitoneal administration The experimental animals used were male mice (Gassner, NMRI) of body weight 20–26 g. 5 animals were tested in each group. The compounds were suspended in 1% strength methylhydroxyethylcellulose and administered intraperitoneally (i.p.) to the animals in a volume of 10 ml/kg of body weight. The compounds according to the invention were tested in doses of 5, 10 and 20 mg/kg i.p. The control group merely received 10 ml/kg of MH not containing active ingredient i.p.

The componds were administered to the animals 30 minutes before the i.p. administration of tetrabenazine (TBZ). The control group merely received 1% strength MH and TBZ in accordance with the same schedule as that for the animals treated with the test substances.

30 minutes after the TBZ injection (TBZ: 40 mg/kg i.p.), the animals were placed in individual plastic boxes and the ptosis was assessed 1 minute later in accordance with the scheme below:

| Ptosis Index: | |
|---|---|
| Eyes closed = 4 | (100% ptosis) |
| Eyes ¾ closed = 3 | (75% ptosis) |
| Eyes ½ closed = 2 | (50% ptosis) |
| Eyes ¼ closed = 1 | (25% ptosis) |
| Eyes open = 0 | (0% ptosis) |

The dose defined as the $ED_{50}$ is that which reduces the mean ptosis index (maximum 4) by 50%.

The results are compiled in Table 1 below.

C. Inhibition of reuptake of norepinephrine in synaptosomes

Synaptosomes from rat brain were isolated by the method of Whittaker (Handbook of Neurochemistry 2, 327–364, Editor A. Lajtha; London and New York, 1969) and the uptake of monoamine was measured by the method of Schacht and Heptner (Biochemical Pharmac. 23, 3413–3422). The $^{14}C$-norepinephrine uptake was measured in a Krebs-Henseleit bicarbonate buffer pH 7.4 which contained 11 millimoles of glucose. 2.5 ml of the suspension of synaptosomes were incubated with labeled norepinephrine at 37° C. in the presence or absence of the test substance. The incubation time was 4 minutes. Further uptake was then stopped by cooling in ice. In order to exclude non-specific adsorption, control samples were incubated at 0° C. under otherwise identical conditions.

The amounts of norepinephrine taken up were measured using the membrane filtration technique using a Millipore sampling manifold with cellulose nitrate filters of 25 mm diameter and 0.6 micrometer pore size. The synaptosomes were collected under reduced pressure and the radioactivity was determined in a Packard Tricarb scintillation counter. The amount of collected norepinephrine has been reported as a percentage of the radioactivity which was added to the incubation mixture.

The $IC_{50}$ values (inhibition concentration) in the Table 1 below indicate the concentration of the test substances which show 50% inhibition of the uptake of $^{14}C$-norepinephrine.

The figures obtained in the tests for the toxicity, the tetrabenazine-induced ptosis and the inhibition of reuptake by some compounds according to the invention are compiled in Table 1 below.

TABLE 1

| Compound Example | $ALD_{50}$ mg/kg i.p. | Tetrabenazine-induced ptosis $ED_{50}$ mg/kg i.p. | Inhibition of norepinephrine uptake $IC_{50}$ μmole/l |
|---|---|---|---|
| 2 | 100 | 1.4 | — |
| 3 | 210 | 0.13 | 0.0056 |
| 6 | 100 | 0.79 | 0.0330 |
| 8 | 85 | 0.54 | 0.0100 |
| 11 | 300 | 0.49 | — |
| 13 | 300 | 0.50 | 0.0062 |
| 19 | 40 | 3.30 | 0.050 |
| 20 | 75 | 0.33 | 0.013 |
| 21 | 75 | 0.80 | 0.017 |
| 23 | 55 | 3.0 | — |
| 25 | 28 | 6.59 | — |
| 27 | 27 | 0.53 | — |

The compounds of the general formula I according to the invention and their salts with pharmaceutically tolerated acids have antidepressant activity in a wide dose range. Of course, the level of the dose administered depends on the type of treatment desired, on the nature of the compound and on the condition, the species and the size of the mammal to be treated. On oral administration, satisfactory results are achieved with doses of 0.1–50 mg of active substance per kg of body weight of the animal, while in humans, the daily dose varies between 10 and 400 mg of active substance per subject, preferably between 20 and 200 mg, it being possible to administer single doses of 10–100 mg, preferably once to three times daily. For intravenous or intramuscular use, the dose is 2–150 mg, preferably 5–100 mg, daily.

The compounds can be used alone or mixed with customary pharmaceutical auxiliaries and/or vehicles. For a form of oral use, the compounds are converted by customary methods into suitable forms for administration, such as tablets, hard gelatin capsules or aqueous, alcoholic or oily solutions. Examples of inert vehicles which can be used are magnesium carbonate, lactose or corn starch. Examples of particularly suitable oily vehicles or solvents are vegetable oils, such as olive oil or sunflower oil.

The salts of the compounds according to the invention are formed, for example, with the following acids: hydrochloric, hydrobromic or hydriodic acid, phosphoric acid, sulfuric acid, methyl sulfuric acid, amidosulfonic acid, nitric acid, formic acid, acetic acid, propionic acid, succinic acid, tartaric acid, lactic acid, malonic acid, fumaric acid, oxalic acid, citric acid, malic acid, mucic acid, benzoic acid, salicylic acid, acetylaminoacetic acid, 4,4'-methylene-bis-(3-hydroxy-2-naphthoic acid) (embonic acid), naphthalene-1,5-disulfonic acid, ascorbic acid, phenylacetic acid, p-aminosalicylic acid, hydroxyethanesulfonic acid, benzenesulfonic acid or synthetic resins which contain acid groups, for example those having ion exchanger activity. Examples of suitable solvents for salts of this type are water, physiologic saline solutions or alcohols, such as, for example, ethanol, propanediol or glycerol, but also sugar solutions, such as, for example, glucose or mannitol solutions, or a mixture of the solvents mentioned. Solutions of this type are also suitable for intravenous administration.

Process (a)

EXAMPLE 1

6,7-Dimethoxy-3-(1-methyl-1,2,5,6-tetrahydro-3-pyridyl)-1-phenylisoquinoline 2.8 g of methyl iodide are added to 4.59 g of 6,7-dimethoxy-1-phenyl-3-(3-pyridyl)isoquinoline dissolved in 400 ml of acetone and the solution is stirred at room temperature for 2 days. The precipitate is filtered off and provides 3.5 g of the pyridinium compound, which is dissolved in 300 ml of methanol and 580 mg of sodium hydroxide in 50 ml of water, and 1.1 g of sodium borohydride is added at 0° C. in 2 portions. The mixture is stood overnight at room temperature, the methanol is distilled out in vacuo and the residue is partitioned between toluene and water. 2.5 g of reddish oil are isolated from the dried toluene phase. Chromatography on silica gel using a chloroform/methanol (95:5) mixture provides 2.1 g of pale yellowish resin which is converted by ethanolic hydrochloric acid into 1.75 g of crystalline hydrochloride of melting point 203°–207° C.

The starting material is prepared as follows.

6,7-Dimethoxy-1-phenyl-3-(3-pyridyl)isoquinoline 5.0 g of 3,4-dihydro-6,7-dimethoxy-1-phenyl-3-(3-pyridyl)isoquinoline in 150 ml of diethylene glycol diethyl ether are heated at 160° C. under an atmosphere of nitrogen with 2.5 g of palladium on animal charcoal (10%) for 2.5 hours. The catalyst is filtered off, the solution is evaporated in a rotary evaporator and the residue is washed with ether. 4.0 g of the isoquinoline compound of melting point 176°–177° C. are isolated.

3,4-Dihydro-6,7-dimethoxy-1-phenyl-3-(3-pyridyl)isoquinoline 1.8 g of N-[2-(3,4-dimethoxyphenyl)-1-(3-pyridyl)ethyl]benzamide in 20 ml of phosphorus oxychloride are stirred at 60° C. for 5 hours and at 120° C. for 1.5 hours. The yellow precipitate is filtered off with suction, dissolved in 200 ml of water, and the solution is made alkaline with potassium carbonate and extracted twice with methylene chloride. 1.6 g of dihydroisoquinoline compound of melting point 180°–182° C. are isolated.

N-[2-(3,4-Dimethoxyphenyl)-1-(3-pyridyl)ethyl]benzamide 9.75 g of benzoyl chloride in 10 ml of chloroform are added, cooling in ice, to 14.9 g of 2-(3,4-dimethoxyphenyl)-1-(3-pyridyl)ethylamine and 12.1 g of triethylamine in 200 ml of chloroform. The mixture is stirred at room temperature for 4 hours, the chloroform is distilled out in vacuo and the residue is washed with toluene and water. 18.5 g of the amide of melting point 156°–158° C. are obtained.

2-(3,4-Dimethoxyphenyl)-1-(3-pyridyl)ethylamine 23.1 g of 3,4-dimethoxybenzyl 3-pyridyl ketone in 150 ml of pyridine are converted into the oxime with 12.5 g of hydroxylamine hydrochloride. 16.8 g of oxime of melting point 119°–121° C. are isolated. The oxime is dissolved in 400 ml of isopropanol and 200 ml of methanolic ammonia and hydrogenated with Raney nickel at room temperature. After the theoretical amount of hydrogen has been taken up, the catalyst is filtered off and the solution is evaporated in a rotary evaporator. The oily amine is converted into the amide without further purification.

3,4-Dimethoxybenzyl 3-pyridyl ketone

A mixture of 45.4 g of ethyl nicotinate and 35.4 g of 3,4-dimethoxybenzyl cyanide is added dropwise to a boiling solution of sodium ethylate prepared from 6 g of sodium and 100 ml of ethanol. The mixture is kept at reflux for 5 hours and, after cooling, is poured into 1 liter of water. The excess nicotinic ester is removed with toluene, and the aqueous solution is neutralized with glacial acetic acid, 50.7 g of α-cyano-3,4-dimethoxybenzyl 3-pyridyl ketone separating out as crystals (melting point 149°–152° C.). This cyanoketone (31.0 g) is hydrolyzed in 6N hydrochloric acid at 80°–90° C. The hydrochloride of the 3,4-dimethoxybenzyl 3-pyridyl ketone crystallizes from ethanol with melting point 188°–191° C. and the free base has a melting point of 60°–64° C. The compound is converted into the oxime without further purification.

EXAMPLE 2

3-(1-Ethyl-1,2,5,6-tetrahydro-4-pyridyl)-1-(2-methylphenyl)isoquinoline 4.5 g of 1-(2-methylphenyl)-3-(4-pyridyl)isoquinoline are converted into the N-ethylpyridinium iodide with 2.5 g of ethyl iodide in 50 ml of ethanol. After boiling for 7 hours, the ethanol is distilled out and the residue is dissolved in 200 ml of methanol and 25 ml of water. At room temperature, 1.2 g of sodium hydroxide in 25 ml of water are added, followed by 1.7 g of sodium borohydride in 2 portions. After 6 hours at room temperature, the mixture is worked up and chromatographed as in Example 1. The base (2.8 g) is isolated as a pale oil and converted into the hydrochloride (1.6 g) of melting point 176°–179° C. with ethanolic hydrochloric acid.

The starting material is prepared as follows.

1-(2-Methylphenyl)-3-(4-pyridyl)isoquinoline 37 g of N-[2-phenyl-1-(4-pyridyl)ethyl]-2-methylbenzamide in 800 ml of tetralin are heated with 240 g of phosphorus pentoxide and 60 g of Celite filtration aid, to improve distribution, at 180°–200° C. for 5 hours.

After cooling to 120°–140° C., a further 120 g of phosphorus pentoxide are added and the mixture is heated at 230° C. (reflux) for 16 hours. After cooling, the tetralin is decanted off and the residue is washed several times with toluene. The washed residue is suspended in toluene and water is slowly added with stirring. The aqueous phase is separated off and made highly alkaline with potassium hydroxide. The product is extracted with toluene and, after distilling out the toluene, is chromatographed on silica gel using chloroform/ethyl acetate (8:2). 25 g of oily base are isolated, which provides a hydrochloride of melting point 255°–259° C. with ethanolic hydrochloric acid.

N-[2-Phenyl-1-(4-pyridyl)ethyl]-2-methylbenzamide 48.0 g of 2-methylbenzoyl chloride are added to 56.0 g of 2-phenyl-1-(4-pyridyl)ethylamine and 60 g of triethylamine in 800 ml of chloroform, cooling in ice. The mixture is stirred at room temperature for 2 hours and then washed with sodium bicarbonate solution and water. After drying the chloroform solution, the solvent is distilled out and the oily residue is crystallized with ether. 48 g of amide of melting point 168°–170° C. are isolated.

2-Phenyl-1-(4-pyridyl)ethylamine 5.34 g of benzyl 4-pyridyl ketone and 3.75 g of hydroxylamine hydrochloride in 50 ml of pyridine are heated to boiling for 4 hours. After cooling, the mixture is stirred into 600 ml of water, and the oxime (5.6 g) of melting point 194°–196° C. is filtered off. The oxime is hydrogenated with hydrogen in isopropanol with Raney nickel at 50° C. and under normal pressure. After the customary working up, the amine is obtained as a pale yellow oil.

Benzyl 4-pyridyl ketone

The benzyl magnesium chloride compound is prepared in ether by known methods from 6.6 g of magnesium turnings and 34.2 g of benzyl chloride. While cooling in ice, 26 g of 4-cyanopyridine in 200 ml of ether are added dropwise to the Grignard compound, whereupon a dense mass of crystals is formed which is stirred at room temperature for 20 hours.

The reaction mixture is slowly hydrolyzed with 50 ml of water and 100 ml of 5N hydrochloric acid. The aqueous phase is heated on a steam bath for 1.5 hours, made alkaline with potassium carbonate and extracted with toluene. 5.6 g of the ketone of melting point 94°–96° C. are isolated from the toluene phase after crystallization from ether.

EXAMPLE 3

1-(2-Methylphenyl)-3-(1,2,5,6-tetrahydro-4-pyridyl)isoquinoline 12.5 g of phenyl chloroformate are added dropwise, at 0° C., to 7.7 g of 3-(1-benzyl-1,2,5,6-tetrahydro-4-pyridyl)-1-(2-methylphenyl)isoquinoline and 8.1 g of triethylamine in 150 ml of chloroform. The reaction mixture is stirred at room temperature for 15 hours. After distilling out the solvent, the residue is partitioned between toluene and 0.2N sodium hydroxide solution. The toluene phase is evaporated and the residue in 200 ml of ethanol is hydrolyzed with 200 ml of 10% sodium hydroxide solution at 60° C. for 17 hours. The solvent is again distilled out and the residue in toluene is washed with water. 4.5 g of the amorphous base are isolated, which provides 1.9 g of the hydrochloride of melting point 276°–278° C. with ethanolic hydrochloric acid.

The compounds in Tables 2 and 3 can be prepared in analogy to the examples described above.

TABLE 2

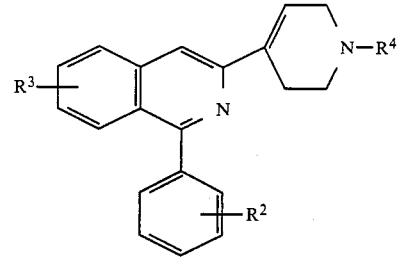

| Example | R⁴ | R² | R³ | Salt | (Melting point °C.) |
|---|---|---|---|---|---|
| 4 | CH₃ | 2-CH₃ | H | Hydrochloride | 290–294 |
| 5 | CH₃ | H | H | Hydrochloride | 195–198 |
| 6 | CH₃ | 2-Cl | H | Hydrochloride | 191–193 |
| 7 | CH₂—C₆H₅ | 2-CH₃ | H | Hydrochloride | 279–281 |
| 8 | CH₃ | 2-F | H | Hydrochloride | 208–211 |
| 9 | C₄H₉ | 2-CH₃ | H | Hydrochloride | 189–193 |
| 10 | CH₃ | H | 6-Cl | Hydrochloride | 320–323 |
| 11 | CH₂—CH=CH₂ | 2-CH₃ | H | Oxalate | 213–215 |
| 12 | CH₂—CH=CH₂ | H | H | Hydrochloride | 260–262 |
| 13 | H | H | H | Hydrochloride | 327 |
| 14 | CH₃ | H | 6,7-di-CH₃O | Hydrochloride | 245–247 |
| 15 | H | H | 6,7-di-CH₃O | Hydrochloride | 278–281 |

TABLE 3

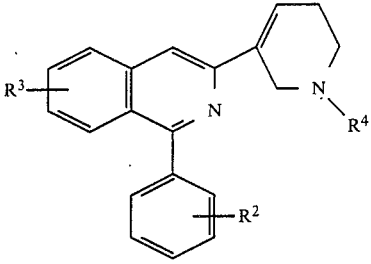

| Example | R⁴ | R² | R³ | Salt | (Melting point °C.) |
|---|---|---|---|---|---|
| 16 | CH₃ | H | 6,7-di-CH₃O | Hydrochloride | 203–207 |
| 17 | CH₂–⌬ | H | 6,7-di-CH₃O | Oxalate | 239–240 |
| 18 | H | H | 6,7-di-CH₃O | Hydrochloride | 224–227 |
| 19 | CH₃ | H | H | Hydrochloride | 219–221 |
| 20 | H | H | H | Hydrochloride | 239–240 |

Process (b)

EXAMPLE 21

1-Phenyl-3-(4-piperidinyl)isoquinoline 7.7 g of 1-phenyl-3-(4-pyridyl)isoquinoline are hydrogenated with 0.5 g of platinum oxide in 800 ml of ethanol at room temperature and under normal pressure for 24 hours. The catalyst is filtered off, the solution is evaporated in a rotary evaporator and the residue is partitioned between chloroform and water. The chloroform solution is evaporated and the residue is dissolved in ether. 1.95 g of 1-phenyl-3-(4-piperidinyl)-1,2,3,4-tetrahydroisoquinoline of melting point 141°–142° crystallize out.

The mother liquor contains 5.6 g of a mixture of substances which are separated by chromatography. 2.8 g of 1-phenyl-3-(4-piperidinyl)isoquinoline are isolated, the hydrochloride of which melts at 238°–242° C.

EXAMPLE 22

1-(2-Methylphenyl)-3-(4-piperidinyl)isoquinoline hydrochloride of melting point 235°–236° C. is obtained from 1-(2-methylphenyl)-3-(4-pyridyl)isoquinoline by a procedure analogous to that described in Example 21.

EXAMPLE 23

3-(1-Allyl-4-piperidinyl)-1-(2-methylphenyl)isoquinoline

Using potassium carbonate, the base is liberated from 1.3 g of 1-(2-methylphenyl)-3-(4-piperidinyl)isoquinoline hydrochloride and is dissolved in 40 ml of toluene. This solution is stirred with 0.82 g of sodium carbonate, 0.1 g of potassium iodide and 0.61 g of allyl bromide at room temperature for 15 hours and then at 50° C. for 2 hours. The reaction mixture is partitioned between toluene and water, and 1.2 g of a pale oil is isolated from the toluene solution, which oil can be converted, with oxalic acid in isopropanol, into 1.4 g of the oxalate of melting point 217°–219° C.

The compounds in Table 4 can be prepared in analogy to the Examples 21–23 described above.

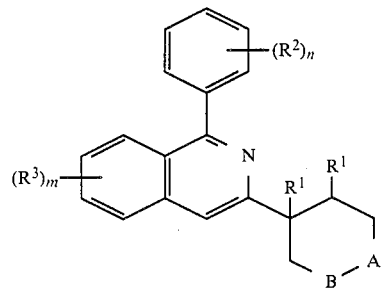

| Example | R⁴ | R² | R³ | Salt | (melting point °C.) |
|---|---|---|---|---|---|
| 24 | —C₂H₅ | H | H | hydrochloride | amorphous |
| 25 | —CH₃ | H | H | hydrochloride | 249–252 |
| 26 | —C₂H₅ | 2-CH₃ | H | hydrochloride | amorphous |
| 27 | —CH₃ | 2-CH₃ | H | hydrochloride | 201–202 |

We claim:

1. A 1-phenylisoquinoline derivative of the formula I in which m and n, independently of one another, denote one or two, one of A and B is CH₂ and other is a N-R⁴ group, R⁴ being hydrogen, benzyl or a straight-chain or branched, saturated or unsaturated C₁-C₆-alkyl radical, and the radicals R¹ denote hydrogen or, together, a bond, and R² denotes hydrogen, halogen, hydroxyl, nitro, amino, C₁-C₆-alkyl or C₁-C₆-alkoxy radicals, and R³ denotes hydrogen, halogen, hydroxyl, nitro, amino, C₁-C₆-alkyl or C₁-C₆-alkoxy radicals, or the benzyloxy, methylenedioxy or ethylenedioxy group.

2. Pharmaceutical composition containing as the active ingredient an effective amount of a 1-phenylisoquinoline derivative of the formula I in claim 1, in admixture or conjunction with a pharmaceutically acceptable carrier and/or constituent.

3. Method for treating depression by administering to the patient an effective amount of a 1-phenylisoquinoline derivative of the formula I in claim 1.

* * * * *

UNITED STATES PATENT AND TRADEMARK OFFICE
CERTIFICATE OF CORRECTION

PATENT NO. : 4,547,508

DATED : October 15, 1985

INVENTOR(S) : KONZ ET AL.

It is certified that error appears in the above-identified patent and that said Letters Patent is hereby corrected as shown below:

Claim 1, line 45, before "other" insert --the--.

Signed and Sealed this

Twenty-eighth Day of January 1986

[SEAL]

Attest:

DONALD J. QUIGG

Attesting Officer

Commissioner of Patents and Trademarks